United States Patent
Zeng et al.

(10) Patent No.: US 12,059,208 B2
(45) Date of Patent: Aug. 13, 2024

(54) ROBOT-ASSISTED HAND-EYE COORDINATION TRAINING SYSTEM BASED ON SMOOTH PURSUIT EYE MOVEMENT AND GUIDANCE FORCE FIELD

(71) Applicant: SOUTHEAST UNIVERSITY, Nanjing (CN)

(72) Inventors: Hong Zeng, Nanjing (CN); Xiao Li, Nanjing (CN); Qingqing Chen, Nanjing (CN); Jianxi Zhang, Nanjing (CN); Aiguo Song, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 18/022,758

(22) PCT Filed: Jun. 28, 2022

(86) PCT No.: PCT/CN2022/101834
§ 371 (c)(1),
(2) Date: Feb. 23, 2023

(87) PCT Pub. No.: WO2023/245696
PCT Pub. Date: Dec. 28, 2023

(65) Prior Publication Data
US 2024/0206728 A1    Jun. 27, 2024

(30) Foreign Application Priority Data
Jun. 23, 2022  (CN) .......................... 202210724205.9

(51) Int. Cl.
*G06K 9/00* (2022.01)
*A61B 3/113* (2006.01)
(Continued)

(52) U.S. Cl.
CPC .............. *A61B 3/113* (2013.01); *A63B 22/00* (2013.01); *G16H 20/30* (2018.01); *A63B 2022/0092* (2013.01)

(58) Field of Classification Search
None
See application file for complete search history.

(56) References Cited

FOREIGN PATENT DOCUMENTS

| | | |
|---|---|---|
| CN | 106504605 A | 3/2017 |
| CN | 106779045 A | 5/2017 |

(Continued)

OTHER PUBLICATIONS

Li (Classification of Eye Movement and Its Application in Driving Based on a Refined Pre-Processing and Machine Learning Algorithm, in IEEE Access, Oct. 2021, pp. 136164-136181) (Year: 2021).*

(Continued)

*Primary Examiner* — Wei Wen Yang
(74) *Attorney, Agent, or Firm* — Bayramoglu Law Offices (57) ABSTRACT

A robot-assisted hand-eye coordination training system based on a smooth pursuit eye movement and a guidance force field includes a virtual interactive scene module, a smooth pursuit eye movement detection module, a robot-assisted interception module and an impact force rendering module. The virtual interactive scene module can generate a virtual interactive scene having a virtual moving object and a virtual handle agent. The smooth pursuit eye movement detection module collects an eye movement signal of a user when the user performs pursuit eye movements on the virtual moving object to detect a smooth pursuit eye movement event. The robot-assisted interception module estimates a movement direction of the virtual moving object, generates an interception and guidance force field, and therefore generates assisting force to assist the user in (Continued)

interception. The impact force rendering module generates impact force according to an impact force computation model after collision is detected.

9 Claims, 2 Drawing Sheets

(51) Int. Cl.
    *A63B 22/00*     (2006.01)
    *G16H 20/30*     (2018.01)

(56) References Cited

FOREIGN PATENT DOCUMENTS

| | | | | |
|---|---|---|---|---|
| CN | 107519622 A | | 12/2017 | |
| CN | 111890389 A | * | 11/2020 | ............ B25J 13/00 |
| CN | 112891137 A | | 6/2021 | |
| CN | 113633937 A | | 11/2021 | |
| WO | 2012165882 A2 | | 12/2012 | |
| WO | WO-2018237172 A1 | * | 12/2018 | |

OTHER PUBLICATIONS

Li (Year: 2021).*

* cited by examiner

ROBOT-ASSISTED HAND-EYE COORDINATION TRAINING SYSTEM BASED ON SMOOTH PURSUIT EYE MOVEMENT AND GUIDANCE FORCE FIELD

CROSS REFERENCE TO THE RELATED APPLICATIONS

This application is the national phase entry of International Application No. PCT/CN2022/101834, filed on Jun. 28, 2022, which is based upon and claims priority to Chinese Patent Application No. 202210724205.9, filed on Jun. 23, 2022, the entire contents of which are incorporated herein by reference.

TECHNICAL FIELD

The present disclosure relates to a robot-assisted hand-eye coordination training system based on a smooth pursuit eye movement and a guidance force field, and belongs to the fields of rehabilitation training and motor learning.

BACKGROUND

A stroke is an acute vascular disease that can damage brain tissues because a blood vessel in the brain bursts and get blocked briefly or permanently, and blood cannot flow into the brain in time consequently. It has a high incidence, a high disability rate, a high mortality rate, a high recurrence rate and substantial economic burden, and has always been regarded as one of the main causes of death and disability in the world. Patients with a cerebral stroke can have limb dysfunction due to different lesion sites, among which, poor eye-hand coordination is a common one. As for the hand-eye coordination, it is a kind of ability that the brain can respond in time and send out control signals to control hand muscles to make corresponding actions after information received by eyes is transmitted to the brain through nerves, which reflects coordination and stability of a human nervous system and the cooperation ability between hands and the eyes. Although the tissue damage caused by the stroke is irreversible, related research shows that some limb functions can be recovered through the plasticity of the brain. After conventional treatment, targeted rehabilitation training can play a very important role in the rehabilitation process of patients. Traditional rehabilitation training methods mainly depend on professional rehabilitation therapists who teach the patients to perform rehabilitation training. During the training process, what the patients can do is to passively go on rehabilitation training following an arrangement of the therapists, and they can get bored. Besides, the training effects and solutions rely on subjective judgment of the therapists to a great extent, which requires the rehabilitation therapists to have high professional quality. However, professional therapists are often in short supply in the case of a great patient population. In order to solve the problem that the rehabilitation training patients vastly outnumber the therapists, people turn their attention to the research and development of robot-assisted upper limb training systems to replace accompanying training by the therapists for the patients. The upper limb training robot system generally consists of a robot itself and supporting virtual interactive scenes, in which the robot provides power for patients, and the virtual interactive scenes provide varied training tasks and visual feedback.

It is found through research that in the process of robot-assisted upper limb training of a user, the auxiliary training combined with a movement intention of the user can effectively stimulate the a motor cortex of the brain, accelerate remodeling of nerve functions and improve the training efficiency. As an important human body sensory organ, eyes can be used to get a mass of external information, and their movements can reflect movement intentions. They can not only receive information, but also serve as information input channels to reflect the movement intentions. Before people operate some moving objects, their eyes will smoothly pursue the moving objects to obtain their related movement information for facilitating related operation. Compared with a method of obtaining a movement intention of the user through electroencephalogram (EEG) or electromyography (EMG), the method of eye movements is more convenient and simple, and can be implemented merely with an eye tracker. However, EEG requires electrical joint compound applying and EEG cap wearing in advance, and for EMG, electrode sticking to target muscles in advance is required.

SUMMARY

To solve the above problems, the present disclosure discloses a robot-assisted hand-eye coordination training system based on a smooth pursuit eye movement and a guidance force field. An eye movement signal is collected and is detected for a smooth pursuit eye movement event, such that a movement direction of a virtual moving object in a virtual interactive scene is estimated to obtain a movement intention of a user, and an interception and guidance force field is generated to assist the user in completing a training task, thereby training hand-eye coordination.

In order to achieve the above objective, the present invention provides the following technical solution:

A robot-assisted hand-eye coordination training system based on a smooth pursuit eye movement and a guidance force field, configured to assist a user in rehabilitation training with a robot handle of an upper limb rehabilitation robot, and comprising a virtual interactive scene module, a smooth pursuit eye movement detection module, a robot-assisted interception module and an impact force rendering module, wherein the virtual interactive scene module can generate a virtual interactive scene for hand-eye coordination training, the virtual interactive scene having a virtual moving object that can provide visual movement stimulation for the user and a virtual handle agent matching movement of the robot handle;

the smooth pursuit eye movement detection module computes an eye movement angular speed of the user by collecting an eye movement signal of the user when the user pursues the virtual moving object in the virtual interactive scene, and classifies an eye movement event according to a computed eye movement angular speed, so as to detect a smooth pursuit eye movement event and transmits a detected smooth pursuit eye movement event to the robot-assisted interception module;

the robot-assisted interception module estimates a movement direction of the virtual moving object in the virtual interactive scene according to the smooth pursuit eye movement event detected by the smooth pursuit eye movement detection module, and generates an interception and guidance force field to generate assisting force to assist the user in pushing the robot handle; and the impact force rendering module obtains a position of the virtual handle agent in the virtual interactive scene by collecting kinematics information of the robot handle, and determines whether the virtual handle agent collides with the virtual moving object by comparing a position of the virtual moving object with the position of the virtual handle agent in the virtual interactive scene, and when it is determined that the virtual handle agent successfully intercepts the virtual moving object, feedback force matching impact force is applied to hands of the user by computing the impact force generated when the virtual handle agent collides with the virtual moving object.

As an improvement of the present invention, the smooth pursuit eye movement detection module comprises an eye movement signal collection module, an eye movement signal preprocessing module, an eye movement angular speed computation module and an eye movement event classification module, wherein the eye movement signal collection module is configured to collect the eye movement signal of the user in real time and transmit same to the eye movement signal preprocessing module;

the eye movement signal preprocessing module is configured to eliminate an invalid signal in the eye movement signal transmitted by the eye movement signal collection module and perform filtering and denoising;

the eye movement angular speed computation module can compute the eye movement angular speed $\omega$ according to the eye movement signal, a computation formula for the eye movement angular speed being as follows:

$$\omega = \frac{180}{\pi t} \cdot 2 \cdot \arctan\frac{\sqrt{a^2(x_i - x_{i-1})^2 + b^2(y_i - y_{i-1})^2}}{2l}$$

wherein $(x_i, y_i)$ represents coordinates of a current sampling point, $(x_{i-1}, y_{i-1})$ represents coordinates of a previous sampling point, a represents a width of a display interface, b represents a height of the display interface, l represents a vertical distance from eyes of the user to the display interface, and t represents a sampling period of the eye movement signal; and the eye movement event classification module can classify, based on an IVVT classification method, the eye movement event of the user according to the eye movement angular speed, so as to detect the smooth pursuit eye movement event from the eye movement event of the user.

As an improvement of the present invention, the eye movement signal collection module uses an eye tracker to collect the eye movement signal of the user.

As an improvement of the present invention, two speed thresholds $\omega_{th\_fix}$ and $\omega_{th\_sac}$ are preset in the eye movement event classification module, and when an eye movement angular speed $\omega$ of the current sampling point computed by the eye movement angular speed computation module satisfies $\omega_{th\_fix} < \omega < \omega_{th\_sac}$, the current sampling point is marked with smooth pursuit.

As an improvement of the present invention, the robot-assisted interception module comprises a movement direction estimation module and an interception and guidance force field generation module, wherein the movement direction estimation module estimates a movement track (x, y) of the virtual moving object in the virtual interactive scene by using a unitary linear regression method, obtains the movement direction of the virtual moving object according to an estimated movement track, and transmits an obtained movement direction of the virtual moving object to the interception and guidance force field generation module, the movement track (x, y) of the virtual moving object satisfying:

$$y = \alpha + \beta x$$

wherein $\alpha$ and $\beta$ represent a regression constant and a regression coefficient respectively, and are obtained through least square fitting, x represents an x-coordinate of the virtual moving object, and y represents a y-coordinate of the virtual moving object; and the interception and guidance force field generation module generates the interception and guidance force field according to an estimated movement direction of the virtual moving object, and generates the assisting force to assist the user in operating the robot handle to intercept the virtual moving object in the virtual interactive scene, the interception and guidance force field being expressed as follows:

$$F_{assist} = \begin{cases} F_m, & d \geq d_m \\ k(d - d_0), & d_0 < d < d_m \\ 0, & d \leq d_0 \end{cases}$$

wherein $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a vertical distance from a boundary between the interception and guidance force field and a free interception area to the movement track of the virtual moving object, and d represents a critical distance for achieving the maximum assisting force.

As an improvement of the present invention, the impact force rendering module comprises a robot handle kinematics information collection module, a collision detection module, an impact force computation module and an execution module, wherein the robot handle kinematics information collection module is configured to collect, by means of an internal sensor, the handle kinematics information when upper limbs of the user operates the robot handle;

the collision detection module determines whether the handle successfully intercepts the virtual moving object in the virtual interactive scene according to collected handle kinematics information, and when a detection result shows that the handle collides with the virtual moving object, it indicates that the handle successfully intercepts the virtual moving object;

the impact force computation module computes, by means of an impact force computation model, the impact force generated when the handle collides with the virtual moving object, the impact force computation model being expressed as follows:

$$F = m_b \frac{\frac{(m_b - m_p)v_{b0} + 2m_p v_{p0}}{m_b + m_p} - v_{b0}}{\Delta t}$$

wherein F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and $\Delta t$ represents collision duration; and the electric motor execution module generates an electric motor execution control signal according to the impact force computed by the impact force computation module, and controls an electric motor to run to generate the feedback force that reacts on the hands of the user and matches the impact force.

As an improvement of the present invention, the virtual interactive scene module comprises a training scene generation module and a feedback module, wherein the training scene generation module generates the virtual interactive scene for hand-eye coordination training on the basis of a Pygame platform; and the feedback module is configured to provide the virtual moving object having the visual movement stimulation for the user in the virtual interactive scene, and displaying the virtual handle agent matching the movement of the robot handle.

As an improvement of the present invention, the robot-assisted hand-eye coordination training system is implemented according to the following steps:

step 1, collecting the eye movement signal of the user when the user pursues the virtual moving object in the virtual interactive scene, and performing preprocessing, eye movement angular speed computation and eye movement event classification to detect the smooth pursuit eye movement event; and step 2, estimating the movement direction of the virtual moving object by means of the smooth pursuit eye movement event, generating the interception and guidance force field, assisting the user in pushing the robot handle to intercept the virtual moving object in the virtual interactive scene to complete a training task, simultaneously collecting the kinematics information of the robot handle in real time for collision detection to detect whether interception is successful, computing, when the virtual moving object is successfully intercepted, the impact force by means of an impact force computation model, and controlling and generating, by an electric motor, force feedback on the hands of the user.

As an improvement of the present invention, in step 1, a formula for computing the eye movement angular speed is as follows:

$$\omega = \frac{180}{\pi t} \cdot 2 \cdot \arctan \frac{\sqrt{a^2(x_i - x_{i-1})^2 + b^2(y_i - y_{i-1})^2}}{2l}$$

wherein $(x_i, y_i)$ represents coordinates of a current sampling point, $(x_{i-1}, y_{i-1})$ represents coordinates of a previous sampling point, a represents a width of a display interface, b represents a height of the display interface, l represents a vertical distance from eyes of the user to the display interface, and t represents a sampling period of the eye movement signal; and the eye movement event is classified through an IVVT classification method specifically as follows:

setting two speed thresholds $\omega_{th\_fix}$ and $\omega_{th\_sac}$, and when the eye movement angular speed is greater than the speed threshold $\omega_{th\_fix}$ and less than the speed threshold $\omega_{th\_sac}$, marking the current sampling point with smooth pursuit.

As a further improvement of the present invention, the interception and guidance force field in step 2 is expressed as follows:

$$F_{assist} = \begin{cases} F_m, & d \geq d_m \\ k(d - d_0), & d_0 < d < d_m \\ 0, & d \leq d_0 \end{cases}$$

wherein $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a vertical distance from a boundary between the interception and guidance force field and a free interception area to the movement track of the virtual moving object, and $d_m$ represents a critical distance for achieving the maximum assisting force; and the impact force computation model is expressed as follows:

$$F = m_b \frac{\frac{(m_b - m_p)v_{b0} + 2m_p v_{p0}}{m_b + m_p} - v_{b0}}{\Delta t}$$

wherein F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and $\Delta t$ represents collision duration.

Based on the above technical purpose, compared with the prior art, the present disclosure has the following advantages:

(1) The system may easily estimate the movement direction of the virtual moving object in the virtual interactive scene in a convenient manner by detecting the smooth pursuit eye movement event of the user, so as to obtain the movement intention of the user.

(2) The system may generate the assisting force by generating the interception and guidance force field to help the user with poor hand-eye coordination intercept the virtual moving object better and more accurately, and exercise the hand-eye coordination.

(3) The system uses impact force rendering to generate impact force feedback when the user successfully intercepts the virtual moving object, and therefore increases fidelity of the hand-eye coordination training system and the immersion in the training process.

(4) The hand-eye coordination training system uses the virtual interactive scene to improve enthusiasm and interest of participation of the user in the hand-eye coordination training.

DETAILED DESCRIPTION OF THE EMBODIMENTS

Technical solutions in examples of the present disclosure will be clearly and completely described below with reference to accompanying drawings in the examples of the present disclosure. Apparently, the described examples are merely some examples rather than all examples of the present disclosure. The following description of at least one illustrative example is merely illustrative in nature, and is in no way intended to limit the present disclosure and an application or use thereof. Based on the examples of the present disclosure, all the other examples derived by those of ordinary skill in the art without creative efforts shall fall within the protection scope of the present disclosure. Unless otherwise described particularly, relative arrangements, expressions and values of components and steps set forth in these examples do not limit the scope of the present disclosure. Technologies, methods and apparatuses known to those of ordinary skill in related fields cannot be discussed in detail, but in appropriate cases, the technologies, methods and apparatuses should be regarded as a constituent part of the authorized description. In all examples shown and discussed herein, any specific value should be constructed as merely illustrative, but not limitative. Therefore, other instances of illustrative examples can have different values.

A training task in the present disclosure usually refers to a complex sports task such as playing table tennis and badminton that requires hand-eye coordination in daily life. Herein, a therapist/technician informs a subject of a moving target, and the subject may pursue a movement of the target with eyes thereof, and push a robot handle with hands to intercept the target, so as to complete a training task.

Figure 1:
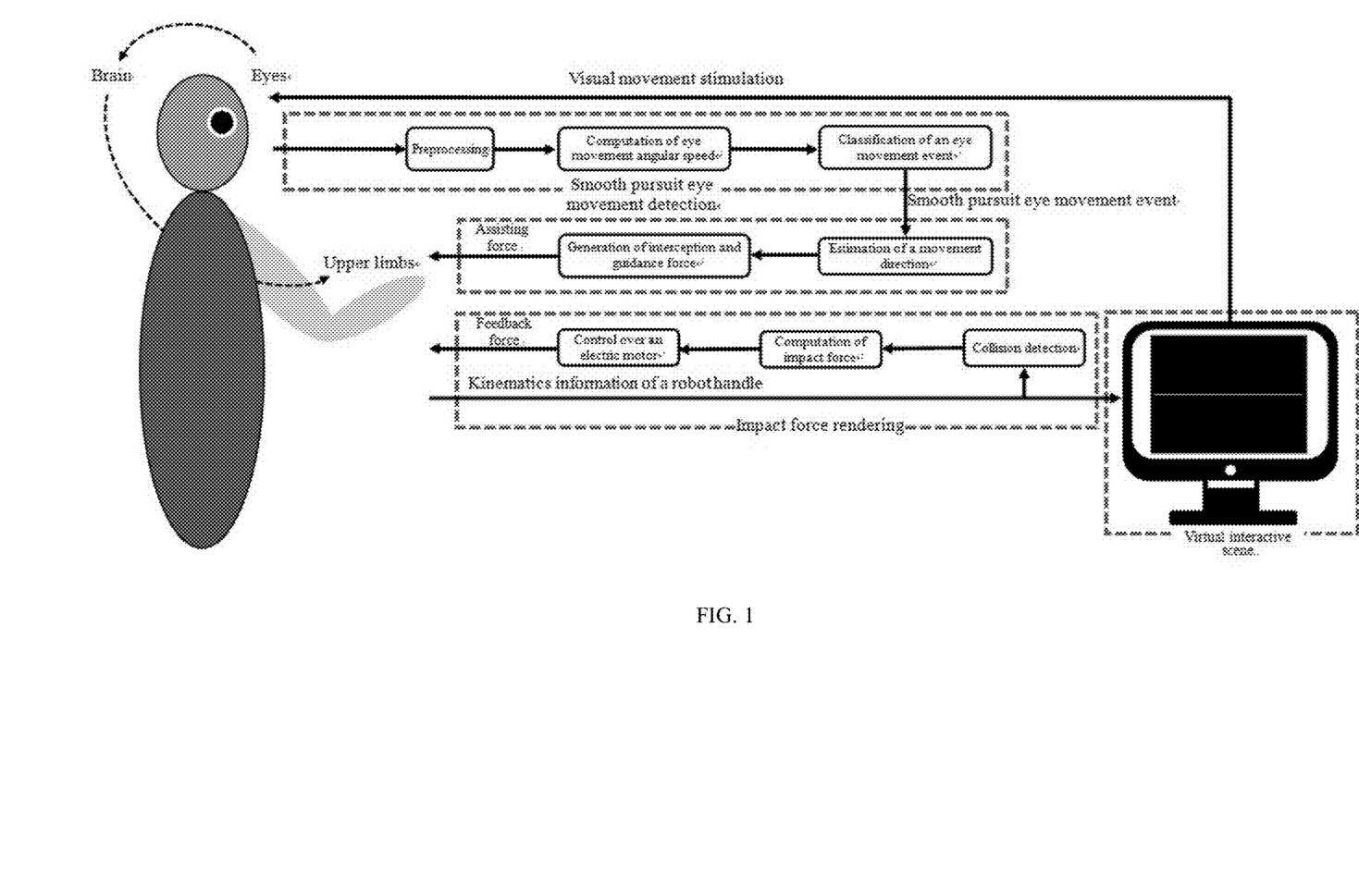
FIG. 1 is a block diagram of a system of the present disclosure.

As shown in FIG. 1, a robot-assisted hand-eye coordination training system based on a smooth pursuit eye movement and force feedback provided by the example of the present disclosure includes:

(1) an eye movement signal of a user when performing pursuit eye movements on a virtual moving object in a virtual interactive scene is collected and is detected for a smooth pursuit eye movement event.

The eye movement signal collected by an eye tracker is subjected to invalid signal removing and Kalman filtering, an eye movement angular speed is computed, and an eye movement event is classified according to the eye movement angular speed, so as to detect the smooth pursuit eye movement event.

The eye tracker uses Pupil Core eye tracker of Pupil Labs Company in Berlin, Germany.

The eye movement angular speed is computed as follows:

$$\theta = \frac{180}{\pi} \cdot 2 \cdot \arctan \frac{\sqrt{a^2(x_i - x_{i-1})^2 + b^2(y_i - y_{i-1})^2}}{2l}$$

where θ represents a rotation angle, relative to a previous sampling point, of a current sampling point of the collected eye movement signal of the user, $(x_i, y_i)$ represents coordinates of the current sampling point, $(x_{i-1}, y_{i-1})$ represents coordinates of the previous sampling point, a represents a width of a display interface, b represents a height of the display interface, and l represents a vertical distance from eyes of the user to the display interface.

According to the rotation angle, relative to the previous sampling point, of the eye movement signal of the user at the current sampling point, a rotation angular speed is computed to obtain the eye movement angular speed:

$$\omega = \frac{\theta}{t}$$

where ω represents an eye movement angular speed, θ represents a rotation angle, relative to the previous sampling point, of the collected eye movement signal of the user at the current sampling point, and t represents a sampling period of the eye movement signal.

The eye movement event is classified through an IVVT classification method specifically as follows:

two speed thresholds $\omega_{th\_fix}$ and $\omega_{th\_sac}$ are set, and when the eye movement angular speed is greater than the speed threshold $\omega_{th\_fix}$ and less than the speed threshold $\omega_{th\_sac}$, the current sampling point is marked with smooth pursuit.

Figure 2:
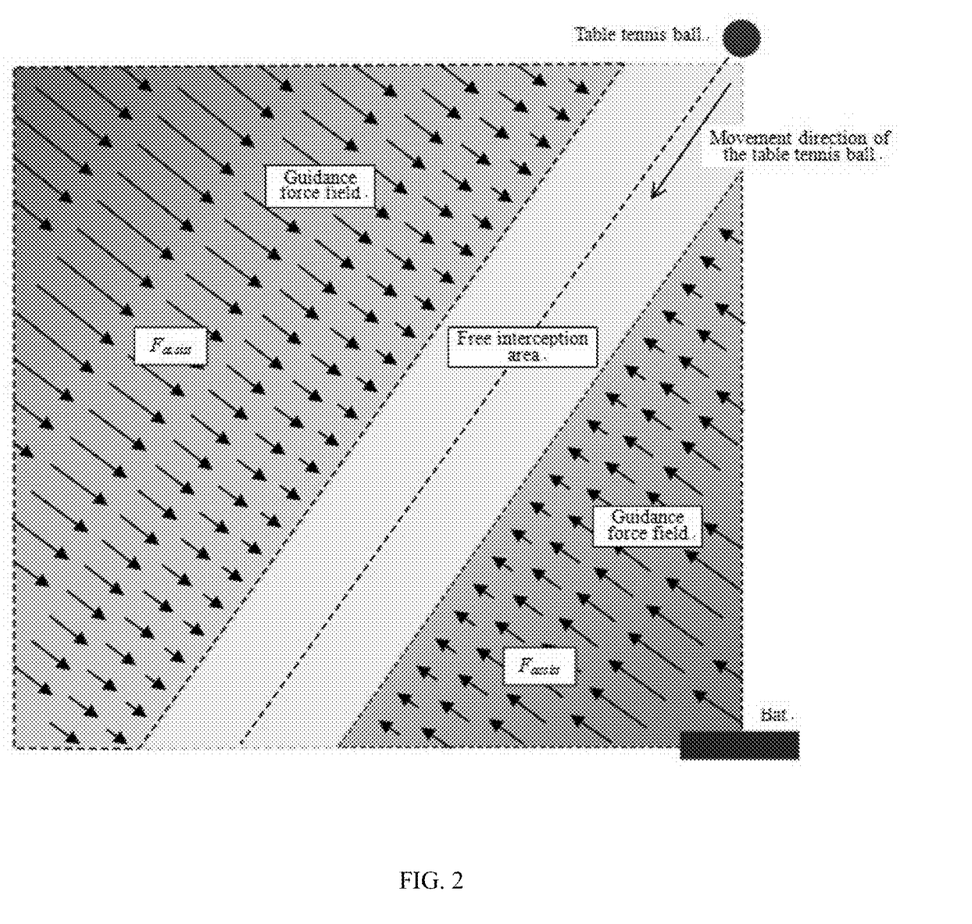
FIG. 2 is a schematic diagram of an interception and guidance force field.

(2) A movement direction of the virtual moving object is estimated, an interception and guidance force field is generated, and therefore assisting force is generated to assist the user in interception, and with reference to FIG. 2, a generated interception and guidance force field is shown.

According to the detected smooth pursuit eye movement event, the movement direction of the virtual moving object is estimated to obtain a movement intention of the user, so as to generate the interception and guidance force field, generate the assisting force to assist the user in pushing the robot handle, and cause the virtual handle agent in the virtual interactive scene to intercept the virtual moving object.

A movement direction estimation module estimates the movement direction of the virtual moving object in the virtual interactive scene based on the detected smooth pursuit eye movement event through the following estimation method:

A movement track of the virtual moving object in the virtual interactive scene is estimated by using a unitary linear regression method:

$$y = \alpha + \beta x$$

where α and β represent a regression constant and a regression coefficient respectively, and are obtained through least square fitting (data for fitting are coordinates of the above sampling points), x represents an x-coordinate of the virtual moving object, and y represents a y-coordinate of the virtual moving object.

The movement direction of the virtual moving object may be obtained according to an estimated movement track.

An interception and guidance force field generation module generates the interception and guidance force field according to an estimated movement direction of the object, and generates the assisting force to assist the user in operating the robot handle of an upper limb rehabilitation robot (ArmMotus™ M2 of), so as to cause the virtual handle agent in the virtual interactive scene to intercept the virtual moving object, the interception and guidance force field being expressed as follows: Shanghai Fourier Intelligence Co., Ltd.

$$F_{assist} = \begin{cases} F_m, & d \geq d_m \\ k(d - d_0), & d_0 < d < d_m \\ 0, & d \leq d_0 \end{cases}$$

where $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a critical distance between absence of the assisting force and presence of the assisting force (that is a vertical distance from a boundary between the interception and guidance force field and a free interception area to the movement track of the virtual moving object), and $d_m$ represents a critical distance (that is, a vertical distance from the virtual handle agent to the movement track of the virtual moving object when the maximum assisting force $F_m$ is reached) for achieving the maximum assisting force $F_m$.

(3) Kinematics information of the robot handle is collected for collision detection, impact force is computed according to an impact force computation model after collision is detected (that is the virtual moving object is successfully intercepted), and an electric motor is controlled to generate force feedback on hands of the user.

When the user pushes the robot handle to make the virtual handle agent intercept the virtual moving object in the virtual interactive scene, an internal sensor of the upper limb rehabilitation robot (ArmMotus™ M2 of Shanghai Fourier Intelligence Co., Ltd.) collects the kinematics information of the robot handle of the user in real time for collision detection. When the virtual handle agent in the virtual interactive scene successfully intercepts the virtual moving object (that is, collision is detected), the impact force is computed based on the impact force computation model, and the electric motor is controlled to generate the impact force feedback on the hands of the user based on DynaLinkHS.CmdJointK-ineticControl control method in SDK (FFTAICommunicationLib) of the upper limb rehabilitation robot above.

Specifically, the impact force computation model is expressed as follows:

$$F = m_b \frac{\frac{(m_b - m_p)v_{b0} + 2m_p v_{p0}}{m_b + m_p} - v_{b0}}{\Delta t}$$

where F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and $\Delta t$ represents collision duration.

(4) Initialization of a training task scene

A two-dimensional table tennis virtual interactive scene is used as the task training scene, and positions and speeds of a table tennis ball and a bat are initialized. In this case, the table tennis ball in the virtual interactive scene is the virtual moving object above, and the bat is the virtual handle agent above. In addition, the present disclosure may also select other training scenes. It is certain that the present disclosure may be more suitable for ball training scenes, such as virtual interactive scenes of tennis and badminton, besides the above virtual interactive scene of table tennis.

(5) Hand-eye coordination training

Through a lot of long-term training, the hand-eye coordination of the subject is constantly exercised. During the training, the moving speed and a moving direction of the table tennis ball may be changed randomly, so as to avoid training effect worsening due to adaptation of the subject.

What is claimed is:

1. A robot-assisted hand-eye coordination training system based on a smooth pursuit eye movement and a guidance force field, configured to assist a user in rehabilitation training with a robot handle of an upper limb rehabilitation robot, and comprising a plurality of modules which comprise computer executable code stored on a non-transitory computer-readable storage medium and configured to perform respective functions in response to execution by at least one processor, the modules including: a virtual interactive scene module, a smooth pursuit eye movement detection module, a robot-assisted interception module and an impact force rendering module, wherein the virtual interactive scene module generates a virtual interactive scene for hand-eye coordination training, the virtual interactive scene having a virtual moving object that provides visual movement stimulation for the user and a virtual handle agent matching movement of the robot handle;

the smooth pursuit eye movement detection module computes an eye movement angular speed of the user by collecting an eye movement signal of the user when the user pursues the virtual moving object in the virtual interactive scene, and classifies an eye movement event according to a computed eye movement angular speed, so as to detect a smooth pursuit eye movement event and transmits a detected smooth pursuit eye movement event to the robot-assisted interception module;

the robot-assisted interception module estimates a movement direction of the virtual moving object in the virtual interactive scene according to the smooth pursuit eye movement event detected by the smooth pursuit eye movement detection module, and generates an interception and guidance force field to generate assisting force to assist the user in pushing the robot handle; and the impact force rendering module obtains a position of the virtual handle agent in the virtual interactive scene by collecting kinematics information of the robot handle, and determines whether the virtual handle agent collides with the virtual moving object by comparing a position of the virtual moving object with the position of the virtual handle agent in the virtual interactive scene, and when it is determined that the virtual handle agent successfully intercepts the virtual moving object, feedback force matching impact force is applied to hands of the user by computing the impact force generated when the virtual handle agent collides with the virtual moving object, wherein the smooth pursuit eye movement detection module comprises an eye movement signal collection module, an eye movement signal preprocessing module, an eye movement angular speed computation module and an eye movement event classification module, wherein the eye movement signal collection module is configured to collect the eye movement signal of the user in real time and transmit same to the eye movement signal preprocessing module;

the eye movement signal preprocessing module is configured to eliminate an invalid signal in the eye movement signal transmitted by the eye movement signal collection module and perform filtering and denoising;

the eye movement angular speed computation module computes the eye movement angular speed ω according to the eye movement signal, a computation formula for the eye movement angular speed being as follows:

$$\omega = \frac{180}{\pi t} \cdot 2 \cdot \arctan\frac{\sqrt{a^2(x_i - x_{i-1})^2 + b^2(y_i - y_{i-1})^2}}{2l}$$

wherein $(x_i, y_i)$ represents coordinates of a current sampling point, $(x_{i-1}, y_{i-1})$ represents coordinates of a previous sampling point, a represents a width of a display interface, b represents a height of the display interface, l represents a vertical distance from eyes of the user to the display interface, and t represents a sampling period of the eye movement signal; and the eye movement event classification module classifies, based on an IVVT classification method, the eye movement event of the user according to the eye movement angular speed, so as to detect the smooth pursuit eye movement event from the eye movement event of the user, and wherein the robot-assisted interception module comprises a movement direction estimation module and an interception and guidance force field generation module, wherein the movement direction estimation module estimates a movement track (x, y) of the virtual moving object in the virtual interactive scene by using a unitary linear regression method, obtains the movement direction of the virtual moving object according to an estimated movement track, and transmits an obtained movement direction of the virtual moving object to the interception and guidance force field generation module, the movement track (x, y) of the virtual moving object satisfying:

$$y = \alpha + \beta x$$

wherein α and β represent a regression constant and a regression coefficient respectively, and are obtained through least square fitting, x represents an x-coordinate of the virtual moving object, and y represents a y-coordinate of the virtual moving object; and the interception and guidance force field generation module generates the interception and guidance force field according to an estimated movement direction of the virtual moving object, and generates the assisting force to assist the user in operating the robot handle to intercept the virtual moving object in the virtual interactive scene, the interception and guidance force field being expressed as follows:

$$F_{assist} = \begin{cases} F_m, & d \geq d_m \\ k(d - d_0), & d_0 < d < d_m \\ 0, & d \leq d_0 \end{cases}$$

wherein $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a vertical distance from a boundary between the interception and guidance force field and a free interception area to the movement track of the virtual moving object, and $d_m$ represents a critical distance for achieving the maximum assisting force.

2. The robot-assisted hand-eye coordination training system based on the smooth pursuit eye movement and the guidance force field according to claim 1, wherein the eye movement signal collection module uses an eye tracker to collect the eye movement signal of the user.

3. The robot-assisted hand-eye coordination training system based on the smooth pursuit eye movement and the guidance force field according to claim 2, wherein two speed thresholds $\omega_{th\_fix}$ and $\omega_{th\_sac}$ are preset in the eye movement event classification module, and when an eye movement angular speed ω of the current sampling point computed by the eye movement angular speed computation module satisfies $\omega_{th\_fix} < \omega < \omega_{th\_sac}$, the current sampling point is marked with smooth pursuit.

4. The robot-assisted hand-eye coordination training system based on the smooth pursuit eye movement and the guidance force field according to claim 1, wherein the impact force rendering module comprises a robot handle kinematics information collection module, a collision detection module, an impact force computation module and an electric motor execution module, wherein the robot handle kinematics information collection module is configured to collect, by means of an internal sensor, the handle kinematics information when upper limbs of the user operates the robot handle;

the collision detection module determines whether the handle successfully intercepts the virtual moving object in the virtual interactive scene according to collected handle kinematics information, and when a detection result shows that the handle collides with the virtual moving object, it indicates that the handle successfully intercepts the virtual moving object;

the impact force computation module computes, by means of an impact force computation model, the impact force generated when the handle collides with the virtual moving object, the impact force computation model being expressed as follows:

$$F = m_b \frac{\frac{(m_b - m_p)v_{b0} + 2m_p v_{p0}}{m_b + m_p} - v_{b0}}{\Delta t}$$

wherein F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and Δt represents collision duration; and the electric motor execution module generates an electric motor execution control signal according to the impact force computed by the impact force computation module, and controls an electric motor to run to generate the feedback force that reacts on the hands of the user and matches the impact force.

5. The robot-assisted hand-eye coordination training system based on the smooth pursuit eye movement and the guidance force field according to claim 3, wherein the virtual interactive scene module comprises a training scene generation module and a feedback module, wherein
the training scene generation module generates the virtual interactive scene for hand-eye coordination training on the basis of a Pygame platform; and
the feedback module is configured to provide the virtual moving object having the visual movement stimulation for the user in the virtual interactive scene, and displaying the virtual handle agent matching the movement of the robot handle.

6. The robot-assisted hand-eye coordination training system based on the smooth pursuit eye movement and the guidance force field according to claim 1, wherein the robot-assisted hand-eye coordination training system is implemented according to the following steps:
step 1, collecting the eye movement signal of the user when the user pursues the virtual moving object in the virtual interactive scene, and performing preprocessing, eye movement angular speed computation and eye movement event classification to detect the smooth pursuit eye movement event; and
step 2, estimating the movement direction of the virtual moving object by means of the smooth pursuit eye movement event, generating the interception and guidance force field, assisting the user in pushing the robot handle to intercept the virtual moving object in the virtual interactive scene to complete a training task, simultaneously collecting the kinematics information of the robot handle in real time for collision detection to detect whether interception is successful, computing, when the virtual moving object is successfully intercepted, the impact force by means of an impact force computation model, and controlling and generating, by an electric motor, force feedback on the hands of the user.

7. The robot-assisted hand-eye coordination training system based on the smooth pursuit eye movement and the guidance force field according to claim 6, wherein in step 1, a formula for computing the eye movement angular speed is as follows:

$$\omega = \frac{180}{\pi t} \cdot 2 \cdot \arctan\frac{\sqrt{a^2(x_i - x_{i-1})^2 + b^2(y_i - y_{i-1})^2}}{2l}$$

wherein $(x_i, y_i)$ represents coordinates of a current sampling point, $(x_{i-1}, y_{i-1})$ represents coordinates of a previous sampling point, a represents a width of a display interface, b represents a height of the display interface, l represents a vertical distance from eyes of the user to the display interface, and t represents a sampling period of the eye movement signal; and
the eye movement event is classified through an IVVT classification method specifically as follows:
setting two speed thresholds $\omega_{th\_fix}$ and $\omega_{th\_sac}$, and when the eye movement angular speed is greater than the speed threshold $\omega_{th\_fix}$ and less than the speed threshold $\omega_{th\_sac}$, marking the current sampling point with smooth pursuit.

8. The robot-assisted hand-eye coordination training system based on the smooth pursuit eye movement and the guidance force field according to claim 6, wherein the interception and guidance force field in step 2 is expressed as follows:

$$F_{assist} = \begin{cases} F_m, & d \geq d_m \\ k(d - d_0), & d_0 < d < d_m \\ 0, & d \leq d_0 \end{cases}$$

wherein $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a vertical distance from a boundary between the interception and guidance force field and a free interception area to the movement track of the virtual moving object, and $d_m$ represents a critical distance for achieving the maximum assisting force; and
the impact force computation model is expressed as follows:

$$F = m_b \frac{\frac{(m_b - m_p)v_{b0} + 2m_p v_{p0}}{m_b + m_p} - v_{b0}}{\Delta t}$$

wherein F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and $\Delta t$ represents collision duration.

9. A robot-assisted hand-eye coordination training system based on a smooth pursuit eye movement and a guidance force field, configured to assist a user in rehabilitation training with a robot handle of an upper limb rehabilitation robot, and comprising a plurality of modules which comprise computer executable code stored on a non-transitory computer-readable storage medium and configured to perform respective functions in response to execution by at least one processor, the modules including: a virtual interactive scene module, a smooth pursuit eye movement detection module, a robot-assisted interception module and an impact force rendering module, wherein
the virtual interactive scene module generates a virtual interactive scene for hand-eye coordination training, the virtual interactive scene having a virtual moving object that provides visual movement stimulation for the user and a virtual handle agent matching movement of the robot handle;
the smooth pursuit eye movement detection module computes an eye movement angular speed of the user by collecting an eye movement signal of the user when the user pursues the virtual moving object in the virtual interactive scene, and classifies an eye movement event according to a computed eye movement angular speed, so as to detect a smooth pursuit eye movement event and transmits a detected smooth pursuit eye movement event to the robot-assisted interception module;

the robot-assisted interception module estimates a movement direction of the virtual moving object in the virtual interactive scene according to the smooth pursuit eye movement event detected by the smooth pursuit eye movement detection module, and generates an interception and guidance force field to generate assisting force to assist the user in pushing the robot handle; and the impact force rendering module obtains a position of the virtual handle agent in the virtual interactive scene by collecting kinematics information of the robot handle, and determines whether the virtual handle agent collides with the virtual moving object by comparing a position of the virtual moving object with the position of the virtual handle agent in the virtual interactive scene, and when it is determined that the virtual handle agent successfully intercepts the virtual moving object, feedback force matching impact force is applied to hands of the user by computing the impact force generated when the virtual handle agent collides with the virtual moving object, wherein the robot-assisted hand-eye coordination training system is implemented according to the following steps:

step 1, collecting the eye movement signal of the user when the user pursues the virtual moving object in the virtual interactive scene, and performing preprocessing, eye movement angular speed computation and eye movement event classification to detect the smooth pursuit eye movement event; and step 2, estimating the movement direction of the virtual moving object by means of the smooth pursuit eye movement event, generating the interception and guidance force field, assisting the user in pushing the robot handle to intercept the virtual moving object in the virtual interactive scene to complete a training task, simultaneously collecting the kinematics information of the robot handle in real time for collision detection to detect whether interception is successful, computing, when the virtual moving object is successfully intercepted, the impact force by means of an impact force computation model, and controlling and generating, by an electric motor, force feedback on the hands of the user, wherein the interception and guidance force field in step 2 is expressed as follows:

$$F_{assist} = \begin{cases} F_m, & d \geq d_m \\ k(d - d_0), & d_0 < d < d_m \\ 0, & d \leq d_0 \end{cases}$$

wherein $F_{assist}$ represents assisting force generated by the interception and guidance force field, $F_m$ represents maximum assisting force generated by the interception and guidance force field, d represents a vertical distance from the virtual handle agent to the movement track of the virtual moving object, k represents an assisting force coefficient, $d_0$ represents a vertical distance from a boundary between the interception and guidance force field and a free interception area to the movement track of the virtual moving object, and $d_m$ represents a critical distance for achieving the maximum assisting force; and the impact force computation model is expressed as follows:

$$F = m_b \frac{\frac{(m_b - m_p)v_{b0} + 2m_p v_{p0}}{m_b + m_p} - v_{b0}}{\Delta t}$$

wherein F represents impact force, $m_b$ represents mass of the virtual moving object in the virtual interactive scene, $m_p$ represents agent mass of the virtual handle agent in the virtual interactive scene, $v_{b0}$ represents a movement speed of the virtual moving object in the virtual interactive scene before collision, $v_{p0}$ represents an agent speed of the virtual handle agent in the virtual interactive scene before collision, and $\Delta t$ represents collision duration.

* * * * *